United States Patent
Yamada et al.

(10) Patent No.: US 6,706,213 B2
(45) Date of Patent: Mar. 16, 2004

(54) PHOSPHOR, RADIATION DETECTOR CONTAINING THE SAME, AND X-RAY CT APPARATUS

(75) Inventors: Hiromichi Yamada, Hino (JP); Tsuneyuki Kanai, Kashiwa (JP); Takaaki Kobiki, Noda (JP); Ichiro Miura, Kashiwa (JP); Makoto Sato, Kashiwa (JP); Minoru Yoshida, Hinode-machi (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/258,543

(22) PCT Filed: Apr. 17, 2001

(86) PCT No.: PCT/JP01/03263
§ 371 (c)(1),
(2), (4) Date: Oct. 25, 2002

(87) PCT Pub. No.: WO01/81500
PCT Pub. Date: Nov. 1, 2001

(65) Prior Publication Data
US 2003/0141484 A1 Jul. 31, 2003

(30) Foreign Application Priority Data
Apr. 26, 2000 (JP) .................................. 2000-125513

(51) Int. Cl.[7] .......................... C09K 11/80; G01T 1/20; A61B 6/03

(52) U.S. Cl. ................ 252/301.4 R; 117/945; 378/4; 250/370.09

(58) Field of Search .............. 250/370.09; 378/4; 117/945; 252/301.4 R

(56) References Cited

U.S. PATENT DOCUMENTS 4,314,910 A * 2/1982 Barnes ............... 252/301.4 R

FOREIGN PATENT DOCUMENTS

EP 467044 * 1/1992
WO WO 99/33934 * 8/1999

* cited by examiner

*Primary Examiner*—C. Melissa Koslow
(74) *Attorney, Agent, or Firm*—Antonelli, Terry, Stout & Kraus, LLP

(57) ABSTRACT

A novel phosphor represented by the general formula

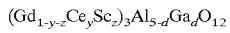

$(Gd_{1-y-z}Ce_y Sc_z)_3 Al_{5-d} Ga_d O_{12}$ (wherein y, z and d are values falling in the ranges of $0.0005 \leq y \leq 0.05$, $0 < z \leq 0.03$ and $0 < d < 5$) is provided by adding scandium (Sc) to a phosphor represented by the general formula of $(Gd_{1-y}Ce_y)_3 Al_{5-d} Ga_d O_{12}$ (wherein y and d are values falling in the ranges of $0.0005 \leq y \leq 0.02$ and $0 < d < 5$). The phosphor has a high luminous efficiency and a very small afterglow. A radiation detector using this phosphor as ceramic scintillator is capable of obtaining a high luminous output and suitable for a radiation detector of X-ray CT because of its high luminous output and a very small afterglow.

12 Claims, 3 Drawing Sheets

PHOSPHOR, RADIATION DETECTOR CONTAINING THE SAME, AND X-RAY CT APPARATUS

BACKGROUND OF THE INVENTION

The present invention relates to a rare-earth element oxide phosphor suitable for use in a radiation detector for detecting X-rays, y rays and the like and particularly for use in the radiation detector of an X-ray CT apparatus, a positron camera or the like. The present invention also relates to a radiation detector and an X-ray CT apparatus using the phosphor.

As the radiation detectors used in X-ray CT apparatuses and the like there have conventionally been used ones combining a xenon gas chamber or BGO (bismuth germanium oxide) single crystal and a photomultiplier tube or combining CsI:Tl single crystal or $CdWO_4$ single crystal and a photodiode. Properties generally required of a scintillator material used in a radiation detector include short afterglow, high luminous efficiency, high X-ray stopping power and chemical stability. The aforementioned single crystal phosphor, however, has variations in its characteristics and drawbacks in any of deliquescence, cleavage, afterglow (emission after X-ray irradiation is stopped) phenomenon, luminous efficiency and the like.

In recent years, however, rare-earth-system phosphors with high radiation-to-light conversion efficiencies have been developed as scintillators and radiation detectors combining such a phosphor with a photodiode have been put into practical use. Rare-earth phosphors consist of rare-earth element oxide or rare-earth element oxysulfide as base material and an activator as luminescence component. As a rare-earth element oxide phosphor, a phosphor including yttrium oxide or gadolinium oxide as base material has been proposed (Japanese Patent Publication No. 63(1988)-59436, Japanese Unexamined Patent Publication No.3 (1991)-50991, for example). As a rare-earth element oxysulfide phosphor, phosphors including Pr or Ce as the activator have been proposed (Japanese Patent Publication No. 60(1985)-4856).

Although these rare-earth-system phosphors include a phosphor having a good luminous efficiency, sufficient performance cannot always be achieved in such applications as X-ray CT which requires a phosphor having a very short afterglow time (a time required for light to attenuate to $\frac{1}{10}$ after X-ray irradiation is stopped).

For solving this problem, the inventors has developed and proposed phosphors including gadolinium (Gd), aluminum (Al) and gallium (Ga) as base material and cerium (Ce) as luminescence component, which has high X-ray stopping power and good wavelength matching with photodetectors (Japanese Patent Application No.9(1997)-355073, International Patent Application WO99/33934).

An object of the present invention is therefore to provide a phosphor with very short afterglow and high luminous efficiency that is particularly useful as a scintillator in X-ray CT and the like based on the above-mentioned GdAlGa:Ce phosphor. Another object of the present invention is to provide a radiation detector that is equipped with the phosphor and is high in detection efficiency. Another object of the present invention is to provide an X-ray CT apparatus that is equipped with a radiation detector with high luminous efficiency as a radiation detector and can provide high-resolution, high-quality tomographic images.

DISCLOSURE OF THE INVENTION

In order to achieve the foregoing objects, the inventors conducted an intense study aiming at improving properties such as luminous efficiency and afterglow of the GdAlGa:Ce phosphor including Ce as luminescence component and found as a result that luminous efficiency of the above-mentioned GdAlGa:Ce phosphor can be markedly improved by adding a certain amount of scandium (Sc) to the phosphor.

Specifically, the phosphor of the present invention is a phosphor represented by the general formula $$(Gd_{1-x-y}L_xCe_ySc_z)_3Al_{5-d}Ga_dO_{12}$$

where L represents La or Y, and x, y, z and d are values falling in the ranges of $0 \leq x < 0.2$, $0.0005 \leq y \leq 0.05$, $0 < z \leq 0.03$, and $0 < d < 5$.

The phosphor of the present invention is a phosphor represented by the general formula $$(Gd_{1-y-z}Ce_ySc_z)_3Al_{5-d}Ga_dO_{12}$$

where y, z and d are values falling in the ranges of $0.0005 \leq y < 0.05$, $0 < z \leq 0.03$, and $0 < d < 5$.

The phosphor of the present invention includes Ce as an activator (luminescence component) and absorbs radiation such as X-rays and gamma rays, exhibits yellowish emission due to Ce ion. When the phosphor is used as a scintillator of a radiation detector, matching with the photodiode is relatively good and a luminous output can be obtained that is 1.8 times or more than that of the $CdWO_4$ currently widely used as a scintillator for X-ray CT. The luminous output is about 1.2 times that of the GdAlGa:Ce phosphor disclosed in Japanese Patent Application No.9(1997)-355073.

The phosphor is markedly low in afterglow since it contains Ce as luminous ion and its emission attenuates to 10% by about 220 ns (nano-seconds) after X-ray irradiation is stopped and to $2 \times 10^{-5}$ by about 30 ms. Generally phosphor afterglow includes primary afterglow and secondary afterglow (long-afterglow component. In X-ray CT, the secondary afterglow is problematic because information-carrying signals (X-ray) become indistinct in the time-axis direction. The phosphor is markedly low in the secondary afterglow (afterglow after 30 ms), i.e., $2 \times 10^{-5}$, and therefore excellent in properties suitable for scintillators of X-ray CT.

In the phosphor of the present invention, part of the element gadolinium (Gd) can be replaced with the element lanthanum (La) and/or the element yttrium (Y). In this case, the phosphor remains markedly low in afterglow. However, the content of La or Y (ratio z replacing Gd) should be less than 0.2, preferably less than 0.1, since as the content increases, the luminous efficiency and X-ray stopping power are degraded. The luminous efficiency and X-ray stopping power can be maximized when La or Y is not included.

Scandium (Sc) markedly improves luminous efficiency of the GdAlGa:Ce phosphor when it is included therein. Specifically, the luminous efficiency becomes about 20% higher than that of the phosphor including no Sc. The effect of Sc can be obtained by adding even a very small amount of Sc. However, if the content (z) of Sc exceeds 0.03, the luminous efficiency lowers to the same level as that of the phosphor including no Sc. Accordingly, the content (z) should be 0.03 or less.

By using aluminum (Al) together with gallium (Ga), high luminous efficiency can be obtained. According to the inventors' investigation, it was found that when Gd-oxide-system phosphors containing Ce as luminous component include only one of Al and Ga, that is, base material is $Gd_3Al_5O_{12}$ or $Gd_3Ga_5O_{12}$, they do not exhibit practical amount of emission contrary to YAG-system. However, once Al and Ga were coexistent in the phosphor, the phosphor becomes to exhibit emission and, in addition, have markedly low afterglow. The total content of Al (5-d) and Ga (d) is 5 to (Gd+L+Ce+Sc)=3 in atomic ratio, and d satisfies 0<d<5, preferably 1.7<d<3.3, more preferably 2≦d≦3. When the Al content and Ga content are within the range of from 1.7 to 3.3 respectively, a luminous output that is 1.8 times or more than that of the $CdWO_4$ can be obtained.

Ce is an element that serves as an activator (luminescence component) in the phosphor of the present invention. The Ce content for generating Ce emission (y) is 0.0005 or greater, preferably 0.001 or greater. The Ce content (y) is defined as 0.05 or less for applications requiring high luminous output because a luminous output 2 times that of $CdWO_4$ cannot be obtained when the Ce content (y) exceeds 0.05. Preferably, the Ce content (y) is defined as 0.02 or less, more preferably 0.015 or less.

The phosphor of the present invention may contain other elements inevitably included therein. For example, when $Gd_2O_3$ is used as a starting material for manufacturing the phosphor of the present invention, $Gd_2O_3$ having purity of 99.99% may include 5 wtppm or less of such impurities as $Eu_2O_3$, $Tb_4O_7$ and, therefore, the phosphor may include such impurities.

The phosphor of the present invention is not particularly limited with regard to crystal morphology. It may be single crystal or polycrystal. The polycrystal is preferred in view of easiness of producing and small variation in characteristics. The process for producing other phosphors as single crystal reported in J. Appl. Phys., vol.42, p3049 (1971) can be applied as the process for preparing the phosphor of the present invention as single crystal. The phosphor is obtained as a sintered material by hot-pressing (HP) process which adds an appropriate sintering agent to scintillator powder (starting material) and presses it under conditions of a temperature of 1,400–1,700° C., and a pressure of about 300–1,400 atm, or by hot-isostatic pressing (HIP) process under the same condition as that of the HP. This enables the phosphor to be obtained as a dense sintered body of high optical transmittance. Since the phosphor of the present invention is cubic crystal and not anisotropic in refractive index, it becomes to have high optical transmittance when it is made into a sintered body.

The phosphor (scintillator powder) before sintering can be prepared as follows: mixing $Gd_2O_3$, $Ce_2(C_2O_4)_3 \cdot 9H_2O$, $Sc_2O_3$, $Al_2O_3$ and $Ga_2O_3$, for example, as starting material powder in a stoichiometric ratio, occasionally adding an appropriate flux component, and conducting baking in an alumina crucible at a temperature of from 1,500° C. to 1,700° C. for several hours. Using the scintillator powder baked in this way, the sintered body is prepared as aforementioned.

The flux component is added in order to lower the melting temperature of the starting materials and expedite crystallization. As the flux component, $BaF_2$ used for sintering the YAG-system phosphor and potassium compounds such as potassium salts can be used alone or as a mixture. The potassium compounds such as $K_2SO_4$, $KNO_3$, $K_2CO_3$, $K_3PO_4$ are preferable.

The phosphor produced in this manner is dense, high in optical transmittance, and small variations in its characteristics. A radiation detector of large luminous output can therefore be obtained. Although the phosphor of the present invention can be used in intensifying screens, fluorescent screens, scintillators and other general phosphor applications, it is particularly suitable for use in X-ray CT detectors, which require high luminous output and small afterglow.

The radiation detector of the present invention is equipped with a ceramic scintillator and a photodetector for detecting scintillator emission. The phosphor described in the foregoing is used as the ceramic scintillator. A photodiode such as a PIN photodiode is preferably used as the photodetector. These photodiodes have high sensitivity and short response. Moreover, as they have wavelength sensitivity from the visible light to near infrared region, they are suitable for their good wavelength matching with the phosphor of the present invention.

The X-ray CT apparatus of the present invention is equipped with an X-ray source, an X-ray detector disposed facing the X-ray source, a revolving unit for holding the X-ray source and the X-ray detector and revolving them about the object to be examined, and image reconstruction means for reconstructing a tomographic image of the object based on the intensity of the X-rays detected by the X-ray detector, which CT apparatus uses as the X-ray detector a radiation detector combining the aforesaid phosphor and a photodiode.

High-quality, high-resolution images can be obtained by utilizing this X-ray detector because the high X-ray detection rate makes it possible to achieve an approximate doubling of sensitivity compared with an X-ray CT apparatus using a conventional scintillator (such as $CdWO_4$) and also because its afterglow is extremely small.

BEST MODE FOR CARRYING OUT THE INVENTION

The X-ray CT apparatus equipped with the radiation detector of the present invention will now be explained with reference to an embodiment.

Figure 1:
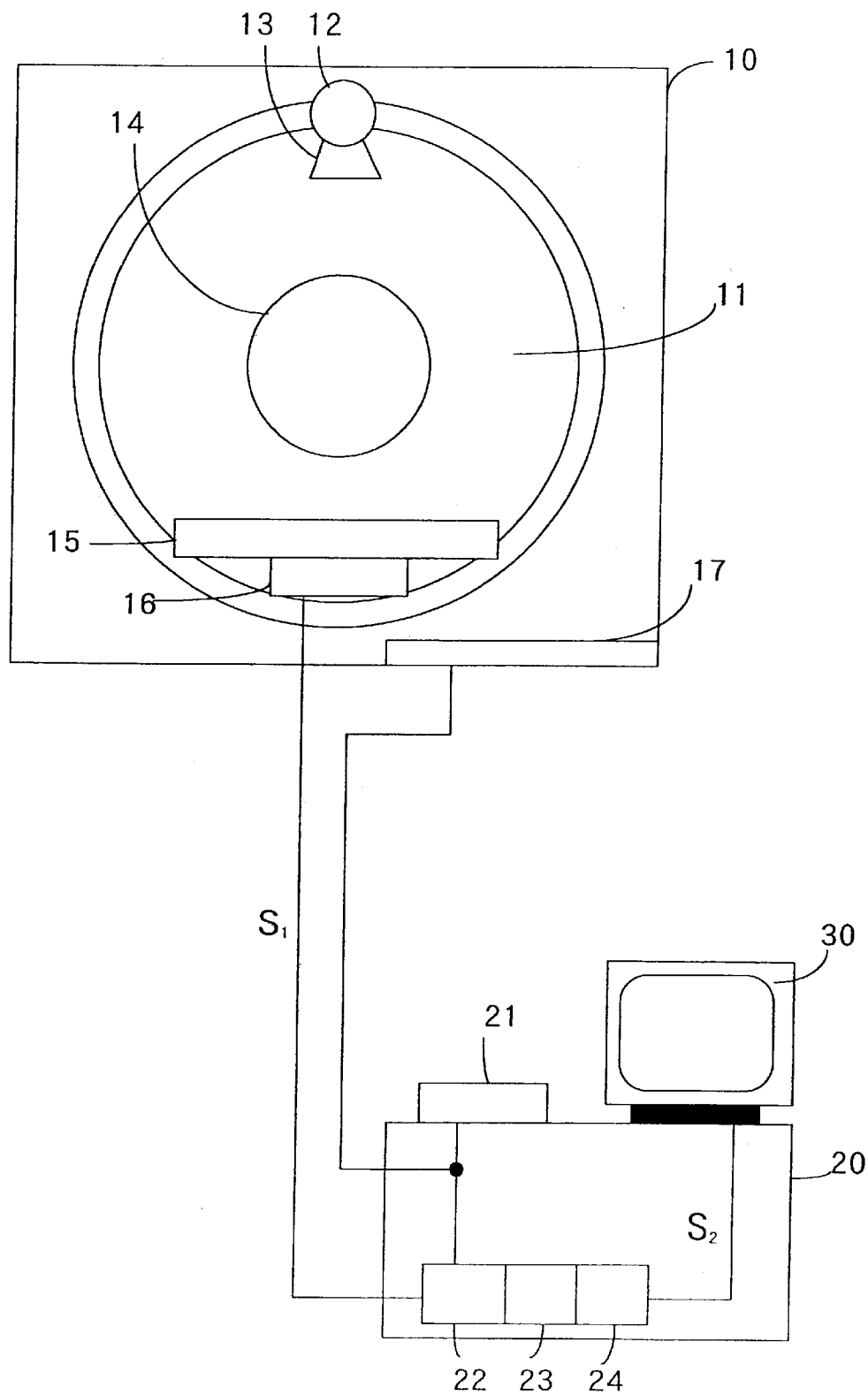
FIG. 1 is a diagram showing the configuration of an X-ray CT apparatus that is an embodiment of the present invention.

FIG. 1 is a schematic view of an X-ray CT apparatus of the present invention. The apparatus comprises a scanner gantry section 10 and an image reconstruction section 20. The scanner gantry section 10 comprises a revolving disk 11 having an open section 14 into which the patient (the object to be examined) is conveyed, an X-ray tube 12 mounted on the revolving disk 11, a collimator 13 attached to the X-ray tube 12 for controlling the direction of the X-ray beam, an X-ray detector 15 mounted on the revolving disk 11 to face the X-ray tube 12, a detector circuit 16 for converting the X-rays detected by the X-ray detector 15 into a prescribed signal, and a scan control circuit 17 for controlling revolution of the revolving disk 11 and the width of the X-ray beam.

The image reconstruction section 20 comprises an input device 21 for inputting the patient's name, date and time of the examination, examination conditions and the like, an image processing circuit 22 for processing measurement data S1 sent from the detector circuit 16 to effect CT image reconstruction, image information adding section 23 for adding to the CT image produced by the image processing circuit 22 the patient's name, date and time of the examination, examination conditions and other information input through the input device 21, and a display circuit 24 for adjusting the display gain of the image-information-added CT image signal S2 and outputting it to a display monitor 30.

X-rays are radiated from the X-ray tube 12 of the X-ray CT apparatus with the patient resting on a table (not shown) installed in the open section 14 of the scanner gantry section 10. The X-rays are imparted directivity by the collimator 13 and are detected by the X-ray detector 15. By revolving the revolving disk 11 around the patient at this time, the X-rays are detected while changing the direction of the X-ray beam. In the case of a full scan, one scan is defined as one rotation (360 degrees) of the revolving disk. The image of one slice is reconstructed from the measurement data for one scan. The tomographic image produced by the image reconstruction section 20 is displayed on the display monitor 30.

Figure 2:
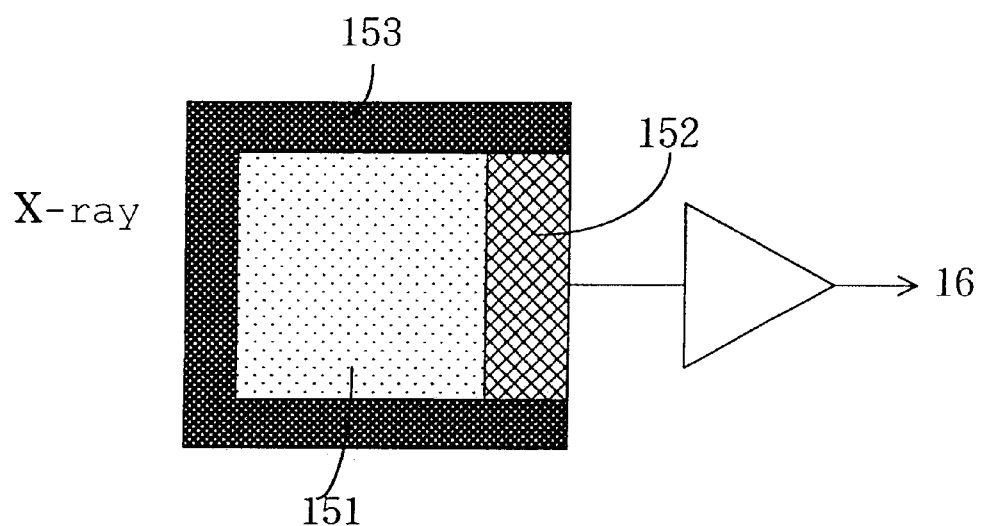
FIG. 2 is a diagram showing the structure of a radiation detector (X-ray detector) that is an embodiment of the present invention.

The X-ray detector 15 has many (e.g., 960) scintillator elements, each a combination of a scintillator and a photodiode, disposed in an arcuate array. As shown in FIG. 2, each scintillator element has a structure combining a scintillator 151 and a PIN photodiode 152, and the p-layer side of the PIN photodiode 152 is connected to the detector circuit 16. The whole element other than the p-layer of the PIN photodiode 152 is covered by a shield 153 to prevent light emitted by the scintillator 151 from escaping to the exterior. The shield 153 is made of a material such as aluminum that passes X-rays and reflects light.

The scintillator 151 is a phosphor that emits light upon absorbing X-rays reaching it from the X-ray tube 12 after passing through the patient. It consists of the phosphor of the present invention. The scintillator 151 is higher in luminous output than conventional scintillators. Moreover, since its emission has emission peaks straddling the high-photosensitivity wavelength region of the PIN photodiode 152, it is photoelectrically converted by the PIN photodiode 152 with high efficiency.

During the taking of tomographic images with this configuration, the X-ray tube 12 continuously emits a fan beam of X-rays as the X-ray tube executes one revolution about once every 1 second to 4 seconds. During this period, the X-rays passing through the object are detected, with the detector circuit 16 side being turned ON and OFF several hundred times. An X-ray detector 15 with high output and short afterglow is therefore required. As the X-ray CT apparatus of the invention utilizes an X-ray detector 15 with high output and low afterglow, it can provide high-quality CT images. Owing to the high luminous output, moreover, the same image can be obtained with a smaller amount of X-rays, whereby the X-ray dosage received by the patient can be reduced.

Although the foregoing explanation with reference to the drawing was made regarding an X-ray CT apparatus using an X-ray tube, the X-ray source is not limited to an X-ray tube but can instead be a beam-type X-ray device that effects beam scanning.

EXAMPLES

Example 1

$Gd_2O_3$, $Ce_2(C_2O_4)_3 \cdot 9H_2O$, $Sc_2O_3$, $Al_2O_3$ and $Ga_2O_3$ were used as raw materials, and they were mixed with a flux component, potassium sulfate. The mixture was packed in an alumina crucible, and, after covering the crucible, subjected to baking at 1,600° C. for 2 hours. The flux was added in an amount of 0.5 mol to one mol of phosphor to be produced. The baked materials were thoroughly washed with water to remove the flux component and then dried to obtain scintillator powder.

The scintillator powder obtained in this manner was press molded and, then, the molded material was subjected to hot pressing under the condition of 1500° C. and 300 atm to obtain sintered body having a composition of $(Gd_{0.998-z}Sc_zCe_{0.002})_3Al_3Ga_2O_{12}$.

Figure 3:
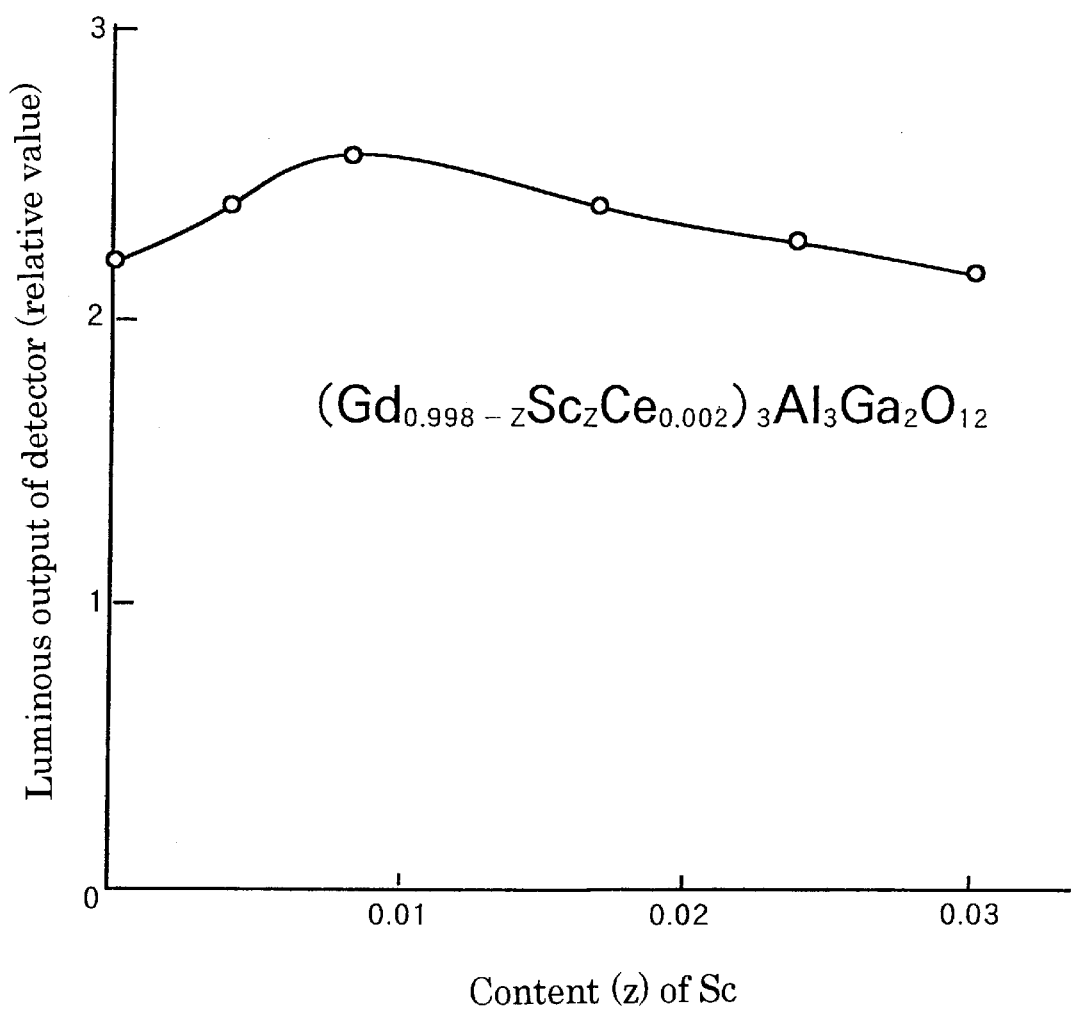
FIG. 3 is a graph showing how detector luminous output varies with Sc concentration in a phosphor of the present invention.

A ceramic scintillator (thickness of 2.5 mm) produced by using the sintered body was combined with a photodiode to produce a detector. The detector was placed at a distance of 15 cm from an X-ray source (120 kV, 0.5 mA), and its luminous output was measured. The results are shown in FIG. 3, which are plotted with luminous output as ordinate and Sc concentration (z) as abscissa. The luminous output was represented with relative values based on the luminous output of a $CdWO_4$ detector defined to be 1.

As clearly seen from the results shown in the figure, luminous output 2.2 times or more than that of the $CdWO_4$ detector could be obtained in the range of Sc concentration (z) 0–0.03, and 2.5 times or more in the Sc concentration (z) of 0.008, which was about 1.2 times that including no Sc.

INDUSTRIAL APPLICABILITY

According to the present invention, there is provided a phosphor having a composition of $(Gd_{1-x-y-z}L_xCe_ySc_z)_3Al_{5-y}Ga_yO_{12}$ and showing high luminous efficiency and very short afterglow. According to the present invention, there is also provided a sintered body having the aforementioned composition and high optical transmittance. A radiation detector comprising this sintered body in combination with a silicon photodiode advantageously shows markedly increased luminous output compared with a conventional detector.

What is claimed is:

1. A phosphor represented by the general formula $$(Gd_{1-x-y-z}L_xCe_ySc_z)_3Al_{5-d}Ga_dO_{12}$$

wherein L represents La or Y, and x, y, z and d are values falling in the ranges of $0 \leq x < 0.02$, $0.0005 \leq y \leq 0.05$, $0 < z \leq 0.03$, and $0 < d < 5$.

2. The phosphor of claim 1, wherein y in the general formula is a value falling in the ranges of $0.0005 \leq y \leq 0.02$.

3. The phosphor of claim 1, wherein x in the general formula is zero.

4. The phosphor of claim 1, wherein d in the general formula is a value falling in the ranges of $1.7 < d < 3.3$.

5. The phosphor of any one of claims 1–4, wherein the phosphor is polycrystal.

6. The phosphor of claim 5, wherein the phosphor is a sintered material obtained by mixing starting material powders in a stoichiometric ratio, baking the starting material powders with flux components and sintering the baked material by hot-pressing or hot-isostatic pressing.

7. A radiation detector comprises a ceramic scintillator and a photodetector for detecting scintillator emission, wherein the phosphor of any one of claims 1–4 is used as the ceramic scintillator.

8. The radiation detector of claim 7, wherein the photodetector is a PIN diode.

9. The radiation detector of claim 7 wherein the ceramic scintillator is polycrystal.

10. The radiation detector of claim 9 wherein the ceramic scintillator is a sintered material obtained by mixing starting material powders in a stoichiometric ratio, baking the starting materials with flux components and sintering the baked material by hot-pressing or hot-isostatic pressing.

11. An X-ray CT apparatus comprising an X-ray source, an X-ray detector disposed facing the X-ray source, a revolving unit for holding the X-ray source and the X-ray detector and revolving them about the object to be examined, and image reconstruction means for reconstructing a tomographic image of the object based on the intensity of the X-rays detected by the X-ray detector, wherein the X-ray detector is a radiation detector of claim 7.

12. The X-ray CT apparatus of claim 11, where in the radiation detector further comprises a PIN diode.

* * * * *